United States Patent [19]

Wakui et al.

[11] Patent Number: 4,555,526

[45] Date of Patent: Nov. 26, 1985

[54] METHOD FOR PRODUCING HYDROCARBONS

[75] Inventors: Tadahiro Wakui, Soka; Tadahiko Handa, Hyogo, both of Japan

[73] Assignee: Daido Sanso K. K., Osaka, Japan

[21] Appl. No.: 630,560

[22] Filed: Jul. 13, 1984

[30] Foreign Application Priority Data

Jul. 15, 1983 [JP] Japan .................. 58-130119

[51] Int. Cl.$^4$ ............................................. C07C 1/04
[52] U.S. Cl. .................... 518/717; 518/713; 518/715
[58] Field of Search ................ 518/717, 715, 713

[56] References Cited

U.S. PATENT DOCUMENTS

| | | | |
|---|---|---|---|
| 2,548,159 | 1/1948 | Houtman | 252/455 |
| 2,573,795 | 11/1951 | Lanning | 518/715 |
| 2,711,420 | 6/1955 | Brown et al. | 518/715 |
| 2,714,116 | 7/1955 | Teichmann et al. | 518/715 |
| 3,933,883 | 1/1976 | Parthanasrothy | 518/715 |
| 4,093,643 | 6/1978 | Vannice | 518/715 |
| 4,151,190 | 4/1979 | Murchison et al. | 518/715 |

*Primary Examiner*—Werren B. Lone
*Attorney, Agent, or Firm*—Armstrong, Nikaido, Marmelstein & Kubovcik

[57] ABSTRACT

Contacting a mixture of hydrogen, carbon monoxide and/or carbon dioxide with an intimate mixture of a carbon monoxide and/or carbon dioxide reducing catalyst such as a Fischer-Tropsch catalyst, and a catalyst carrier comprising a metal oxide having a very narrow pore size distribution in the micropores within the range of between 10 and 100 Angstroms, to produce hydrocarbon mixtures useful in the manufacture of gasoline kerosene and light oil.

7 Claims, 4 Drawing Figures

METHOD FOR PRODUCING HYDROCARBONS

BACKGROUND OF THE INVENTION

This invention relates to a method for producing hydrocarbons by reacting hydrogen gas eith carbon monoxide and/or gaseous carbon dioxide catalytically.

It is well known as the Fischer-Tropsch synthesis from many literatures to produce hydrocarbons by reacting hydrogen with carbon monoxide in the presence of a heterogeneous catalyst. The types of catalysts that have been studied for this and related processes include those based on metals or oxides of iron, cobalt, nickel, ruthenium, rhenium, thorium, rhodium, platinum and osmium. On the other hand, depending upon a catalyst and a reaction condition, the Fischer-Tropsch synthesis can be oriented predominantly to fuel oil, fuel gas such as methane, olefin such as ethylene, waxes or oxygen containing compounds such as alcohols. Consequently, the higher selectivity of desired products is advisable as well as a catalyst have high activity. The distribution of hydrocarbons obtained with a standard catalysts in the Fischer-Tropsch synthesis are fulfilled the Schulz-Flory distribution of molecular weights; the Fischer-Tropsch synthesis is regarded as a kind of polymerization wherein a chain growth occurs by a stepwise addition of active species containing one carbon atom adsorbed on a catalyst surface. Standard Fischer-Tropsch catalysts exhibit a nearly constant chain growth probability, which can be derived from Schulz-Flory plots and is obtained from the relationship between carbon number and the weight fraction of hydrocarbons per the carbon number, that is, these catalysts have low selectivity for the Fischer-Tropsch products. Therefore, it is necessary for us to develop the peculiar Fischer-Tropsch catalysts having non-Schulz-Flory distribution. It is well known from the recent literature (J.C.S. Chem Comm., 1095 (1979)) that Fischer-Tropsch synthesis of hydrocarbons over RuNaY-zeolite which can be prepared by an ion-exchange method shows a drastic change in chain growth probability in comparison with that over the standard Fischer-Tropsch catalysts. Herein, the roll of the zeolite is to control ruthenium metal particle size by cage dimensions in the zeolite. This means that the cage dimensions in the zeolite is used for controlling of the selectivity of Fischer-Tropsch products.

SUMMARY OF THE INVENTION

As the result of our various investigations, it has now been discovered that desirable hydrocarbons from synthesis gas can be selectively obtained by using the heterogeneous catalyst which comprise a metal or a mixture of metals such as ruthenium and iron-potassium oxide supported on a metal oxide such as $\gamma$-alumina and silica gel or mixed metal oxides having an acidic properties such as silica.alumina and silica.magnesia, these carriers having a very narrow pore size distribution in the micropores region within the range of between 10 and 100 Angstroms, in which the pore size of these carriers is slightly larger than that of Y-Zeolite which is the largest in the crystalline aluminosilicates. In other words, it has been found that the chain growth probability suddenly changes to low values over the catalyst supported on an amorphous inorganic metal oxide having a specific pore sizes, the above catalyst showing non-Schulz-Flory product distribution. Thus, it is notable that the selectivity of Fischer-Tropsch products is controlled by the specific pore sizes of the amorphous inorganic metal oxide or mixed metal oxides as a carrier. To be more interesting, a drastic decline in chain growth probability at arbitrary carbon number can be brought depending upon the pore sizes of the above carrier. This means that the gasoline fraction in the vicinity of $C_5$ to $C_{10}$ or the kerosene and light oil fraction in the vicinity of $C_{11}$ to $C_{20}$ can be selectively obtained by using the catalyst carrier described above. The selective formation of the gasoline fraction or the kerosene and light oil fraction in accordance with the present invention can be attributed to an effect exerted by the specific pore sizes of a carrier described in our invention, which has the slightly larger pore than those of conventional crystalline aluminosilicates, that is, the pore sizes within the range of between 10 and 100 Angstroms, and besides which has a very narrow pore size distribution in the micropores range. It may be difficult to obtain selectively the Kerosene and light oil fraction by using even Y-zeolite having the largest pore size in conventional aluminosilicates, that is, the pore size of 11 Angstroms. As noted above, it is considered that the selective formation of the kerosene and light oil fraction in our invention results from the specific pore sizes of a catalyst carrier which has a larger pore size than that of Y-zeolite, and in addition, has a very narrow pore size distribution in the micropores region.

Figure 1:
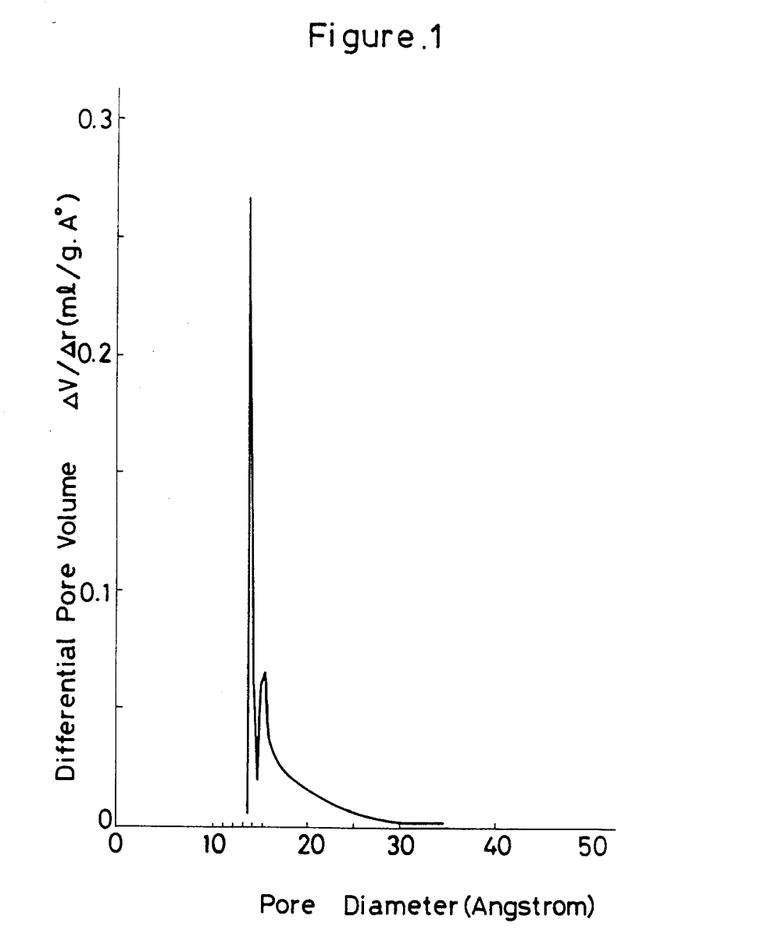
FIG. 1 is a graph of a pore size distribution of a carrier consisting of a metal oxide which was used in this invention.

This invention relates to a novel method for converting synthesis gas to desirable hydrocarbon mixtures in the presence of a particular heterogeneous catalyst. More particularly, the invention relates to a method for converting synthesis gas, that is, a mixture of gaseous carbon monoxide and/or carbon dioxide and hydrogen to hydrocarbon mixtures in the presence of a particular heterogeneous catalyst which comprises a carbon monoxide and/or carbon dioxide reducing VIII group metal supported on a carrier having specific pore sizes in the micropores region. It is an object of the present invention to use a catalyst comprising two components in which the first component is selected from the class of carbon oxides reducing metals in the presence of hydrogen, and the second component is inorganic oxide carriers such as amorphous $\gamma$-alumina and silica gel having specific pore sizes, which are characterized by having a very narrow pore size distribution in the micropores region within the range of between 10 and 100 Angstroms. $\gamma$-alumina and silica gel used as a catalyst carrier in this invention have such a physical property as shown in Table 1. For reference, the pore size distribution of a typical silica gel is shown in FIG. 1 which is the graph with differential pore volume on the vertical axis and average pore diameter horizontally. The surface area of the above samples was measured by means of BET method based on nitrogen adsorption, and the pore volume and the pore size distribution was computed by the nitrogen-desorption method. FIG. 1 shows clearly that the catalyst carriers provided in our invention have a very narrow pore size distribution.

Table 1 also shows clearly that the above carrier is characterized by having a very narrow pore size distribution within the range of between 10 and 100 Angstroms wherein such a pore structure of the above carriers could not be obtained by a conventional production method.

TABLE 1

| Classification of Carrier | Carrier | Acid Treatment | Calcination Temperature °C. | Surface Area m²/g | Pore Volume ml/g | Average Pore Radius Å | Pore Diameter Having the Largest Pore Size Distribution Å |
|---|---|---|---|---|---|---|---|
| A | γ-Alumina | No | 450 | 334 | 0.20 | 11.5 | 13.7 |
|   | γ-Alumina | No | 450 | 396 | 0.28 | 13.8 | 15.7 |
| B | γ-Alumina | No | 550 | 340 | 0.31 | 18.1 | 20.4 |
|   | γ-Alumina | No | 550 | 367 | 0.29 | 17.9 | 18.6 |
| C | γ-Alumina | No | 550 | 260 | 0.30 | 22.9 | 42.1 |
|   | γ-Alumina | No | 550 | 253 | 0.30 | 23.9 | 41.3 |
| D | Silica gel | Yes | 500 | 435 | 0.21 | 9.8 | 13.5 |
|   | Silica gel | Yes | 500 | 526 | 0.24 | 9.1 | 13.4 |
| E | Silica gel | No | 450 | 472 | 0.26 | 10.8 | 14.2 |
|   | Silica gel | No | 450 | 367 | 0.19 | 10.3 | 14.9 |
| F | Silica gel | No | 550 | 367 | 0.24 | 12.8 | 17.3 |
|   | Silica gel | No | 500 | 532 | 0.33 | 12.2 | 15.4 |

DETAILED DESCRIPTION OF THE PREFERRED EMBODIMENTS

In this invention, a mixture of hydrogen with carbon monoxide and/or gaseous carbon dioxide should be used as a starting material. Such a mixture may be effectively prepared by the partial combustion of the materials including carbon and hydrogen. The materials, as used herein include brown coal, anthracite cokes, crude oil and its distillate, tar sands, bituminous coal and lignite. A mixture of hydrogen with carbon monoxide and/or carbon dioxide having the molar ratio ($H_2/CO+CO_2$) of $0.5 \sim 3$ may be used as a starting material.

In accordance with the present invention, the process may be carried out at a temperature of from 200° to 350° C., preferably from 200° to 300° C., and at a pressure of from 0 to 100 Kg/cm²A, preferably from 5 to 30 Kg/cm², and at a gas space velocity of from 500 to 5000 l/hour. The heterogeneous catalysts of this invention comprise 100 parts by weight of a carrier, $0.1 \sim 50$ parts, preferably $0.1 \sim 10$ parts by weight of a VIII group metal or metals, and at least one promoter. The amount of a promoter incorporated with the above metal may be $1 \sim 50$ percent by weight of the above metal. A promoter is necessary for the use of such a catalyst as iron, cobalt and nickel with the exception of ruthenium. It is not or little effective when ruthenium is used in this invention. These promoters used for the catalyst of this invention include various elements such as alkali metals, alkaline earth metals, VIII group metals, Ti, Zr, Al, Si, As, V, Mn, Mo, W, Cu, Ag, Zn, Cd, Bi, Pb, Sn, Ce, Th and U. The most preferable calalyst in this invention is ruthenium supported on γ-alumina or silica gel having the specific pore sizes. The iron catalysts used in this invention consist of iron, potassium and copper supported on γ-alumina or silica gel having the specific pore sizes.

The heterogeneous catalysts may be prepared in various methods. For example, the metal that has catalytic activity for the reduction of carbon monoxide and/or carbon dioxide may be formed on a γ-alumina carrier or a silica gel one having the specific pore sizes by a conventional method such as impregnation of the oxide with salt solutions of the above metal, followed by drying and calcination. Ion exchange of silica gel carrier also may be used in some selected cases to effect the introduction of the carbon monoxide and/or carbon dioxide reducing metal. Other methods for forming the heterogeneous catalysts may be used, such as: precipitation of the carbon monoxide and/or carbon dioxide reducing metal in the presence of a γ-alumina carrier or a silica one; or electrolysis deposition of a metal on a carrier; or deposition of a metal from the vapor phrase; or adsorption of the metal compound or metal compounds such as metal carbonyls on a carrier by dissolving the metal compounds in n-hexane or tetrahydrofuran and adding the carrier to the above solution.

A metal oxide such as γ-alumina and silica gel used as a catalyst carrier in the invention can be prepared from the following starting materials in a water solution. For example, γ-alumina can be produced by reacting an aluminate with an organic compound. Herein, an aluminate which may be used in the invention includes alkali metal salts such as Na, K and Li and ammonium salts. Even the other aluminates can be used, if they are water-soluble. The preferred aluminate is sodium aluminate. Silica gel also can be prepared from a silicate or a mixture of silicic acid and a silicate wherein the silicate includes alkali metal salts such as Na, K and Li and ammonium salts. The preferred starting material for silica gel is a water glass which is a mixture of silicic acid and sodium silicate, with water glass No. 3 particularly preferred. Organic compounds as a starting material include monocarboxylic acid halide, dicarboxylic acid halide and sulfuric acid halide. The preferred organic compounds are mono and di-carboxylic acid halide. The amount of alkali metal as the impurity of the inorganic carriers such as γ-alumina and silica gel which may be used in the invention is preferable not to exceed 0.1 percent by weight.

The inorganic carriers such as γ-alumina and silica gel which are prepared by the method different from the above described particular one can be also used in the invention, if these carriers have a very narrow pore size distribution in the micropores region within the range of between 10 and 100 Angstroms. Thus, the purpose of the invention can be achieved by using both carriers which are prepared by the method described in the invention, and the carriers prepared by other methods if both of the carriers have a very narrow pore size distribution of the micropores within the range of between 10 and 100 Angstroms. The very narrow pore size distribution of the metal oxides used in this invention is distributed preferably 1~30 Angstroms, more preferably, 1~15 Angstroms.

The heterogeneous catalyst can be used in a reactor as a fixed or fluidized bed. Besides, if desired, the above catalyst may be used in liquid phase in which hydrocarbon oil is utilized as a solvent.

Figure 3:
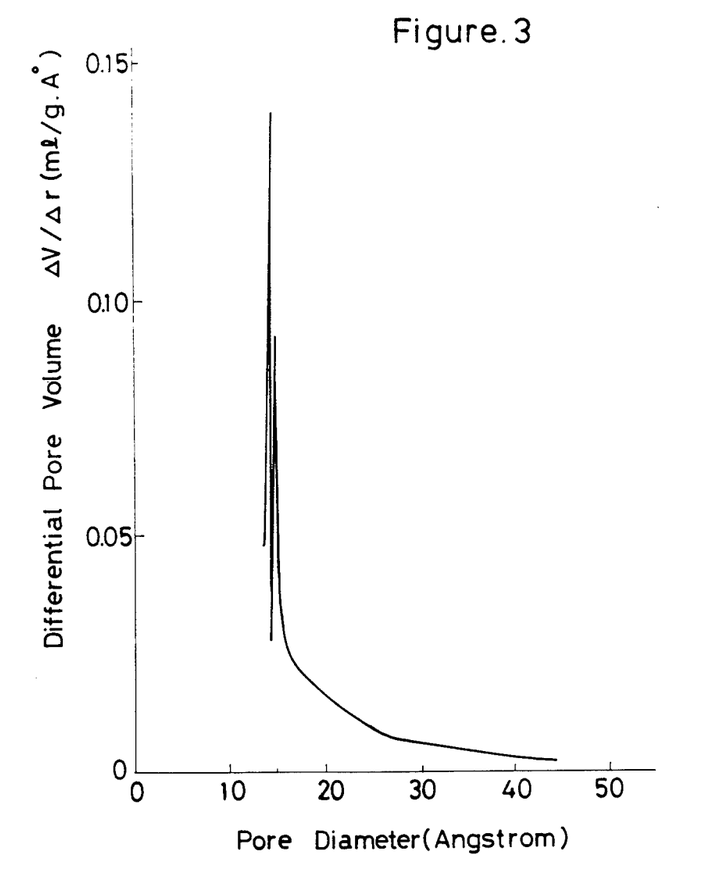
FIG. 3 is a graph of a pore size distribution of a carrier consisting of a metal oxide mixture which was used in this invention.

According to the invention, the formation of hydrocarbons having more than 10 of carbon number may be suppressed; hydrocarbons rich in gasoline boiling range can be obtained, while hydrocarbons having more than 10 of carbon number may be considerably formed by using mixed metal oxides such as usual or conventional silica alumina having wide pore size distribution as a catalyst carrier. To be more interested, it has been found that a drastic decline in chain growth probability of the formed hydrocarbons may be brought by using the heterogeneous catalyst which comprises a metal or a metal oxide having catalytic activity for the Fisher-Tropsch synthesis and a proper amount of an alkali metal supported on an acidic metal oxide mixture described in the invention having a very narrow pore size distribution of the micropores within the range of between 10 and 100 Angstroms in which the pore size of such a carrier is slightly larger than that of conventional crystalline alumino-silicates: the above heterogeneous catalyst shows non-Schulz-Flory product distribution. It is considered that a peculiar product distribution of formed hydrocarbons according to the invention, which can be resulted from the use of the catalyst carriers which have a very narrow pore size distribution within the range of between 10 and 100 Angstroms. Thus this invention relates to a method for producing the desirable hydrocarbons efficiently by using mixed metal oxides as a carrier such as amorphous silica.alumina or silica.magnesia. A silica.alumina as a catalyst carrier has such a pore size distribution representatively shown in FIG. 3, which is the graph with differential pore volume on the vertical axis and average pore diameter horizontally. FIG. 3 shows clearly that the catalyst carriers which may be used in the invention have a very narrow pore size distribution.

In this case, it is desirable to add 0.1~17 parts, preferably 2~8.5 parts by weight of alkali metal to 100 parts by weight of the mixed metal oxides as a catalyst carrier in order to neutralize the acidity of the above mixed metal oxides. Herein, alkali metal described above is different from the promoter mentioned previously which is not necessary for a ruthenium catalyst.

The mixed metal oxides such as silica.alumina or silica.magnesia which may be used as a catalyst carrier in the invention can be prepared by various methods, such as: addition of three components at the same time in the form of solution wherein three components are (1) water-soluble alkali (Na, K and Li) or ammonium salts such as sodium aluminate or water glass consisting of a mixture of silicic acid and silicate, (2) organic compounds such as organic halides and (3) metal salts such as metal nitrates (aluminium nitrate etc.) and metal halides (aluminium chloride etc.); or coprecipitation by adding an organic compound to a water solution of alkali such as sodium aluminate or water glass or ammonium salts, followed by adding a metal salt such as metal nitrates to the former solution before deposition of a solid; or adsorption of hydrogel obtained by adding ammonium solution as a precipitant to a solution of a metal salt, or another hydrogel previously precipitated by reacting a metal acid salt such as alkali or ammonium salts with an organic compound. The organic compounds include monocarboxylic acid halide, dicarboxylic acid halide and sulfuric acid halide, preferably, mono and di-carboxylic acid halide. The amount of alkali metals as the impurity of the metal oxide mixture is preferably not to exceed 0.1 percent by weight especially when the acidity of such carriers is utilized.

The mixed metal oxides which are prepared by the method different from the above-described particular one may be also used as the catalyst carrier in the invention if these carriers have a very narrow pore size distribution in the micropores region within the range of between 10 and 100 Angstroms. Thus this invention relates to a method for producing desirable hydrocarbons by using the calalyst carriers which have a very narrow pore size distribution in the micropores region within the range of between 10 and 100 Angstroms wherein the above-described catalyst carriers include both inorganic oxides which are prepared in the invention and ones prepared by other methods.

The heterogeneous catalyst may be contained as a fixed bed, or a fluidized bed may be used. Besides, if desired, the above catalyst may be used in liquid phase in which hydrocarbon oil is utilized as solvent. The following examples are given to illustrate the present invention.

EXAMPLE 1

Some kinds of heterogeneous catalysts which were supported on γ-aluminas or silica gels were tested for the production of hydrocarbons by the Fisher-Tropsch-synthesis.

Those catalysts carrier or support were prepared by the following method: a γ-alumina was produced as follows; a solution of adipoyl dichloride which was previously dissolved in tetrahydrofuran was added dropwise to an aqueous solution of sodium aluminate with vigorous stirring at 40° C.

After the addition was completed, pH was adjusted to 6~9 with 5% hydrochloric acid and stirring was continued for additional 5 hrs. Then the reaction mixture was cooled, filtered after standing and washed successively an ammonium solution, 10% ammonium chloride solution and distilled water until free of chloride ion. That solid was extracted with acetone to remove entrained organic compound, followed by drying at 110° C. for 3 hours and then by calcinating at 450° C.~550° C. for 5 hours in air. The surface area, the pore volume and the pore size distribution of a γ-alumina which was prepared by the above-described method are shown in Table 1 (Classification of Carrier A). The pore diameter having the largest differential pore volume is also shown in Table 1 because the carriers such as the above-described γ-alumina which is used in the invention have a very narrow pore size distribution in the micropore sizes region. Moreover, γ-aluminas and silica gels, each having various pore sizes, were also prepared by the similar above-noted method except the use of succinoyl dichloride, adipoyl dichloride, sebacoyl dichloride (Classification of Carrier, A and D), sebacyl dichloride, 1,12-dodecanadioyl dichloride (Classification of Carrier B and F), 1,14-dodecanoyl dechloride (Classification of Carrier C and F), phthaloyl, and isophthaloyl, and terephthaloyl dichloride (Classification of Carrier A and B), and dichloride of hydrocarbon oligomer having two terminal carboxylic acid group (the molecular weight is 500~1000) (Classification of Carrier C~F). Representative physical properties of $\gamma$-aluminas and silica gels mentioned above are also shown in Table 1.

CATALYST 1 (Ruthenium/$\gamma$-alumina)

The catalyst was prepared by the following impregnation method: 0.5 gram of ruthenium chloride ($RuCl_3 \cdot H_2O$) was dissolved in 5 ml of water. The resulting solution was added to 10 ml of a $\gamma$-alumina (Classification of Carrier A). After the mixture was allowed to stand overnight at room temperature, it was dried at 110° C. for 3 hours and was calcined at 450° C. in air for 4 hours. The resultant catalyst contained 1.9 parts by weight of ruthenium metal per 100 parts by weight of a $\gamma$-alumina. The catalyst belonging to classification of Carriers B, C and so on (Table 1) were also prepared by the method similar to that described above. Each catalyst contained 1.5~2.2 parts by weight of ruthenium per 100 parts by weight of $\gamma$-alumina.

COMPARATIVE CATALYST 1
(Ruthenium/Alumina)

A comparative catalyst 1 was prepared by the same method as mentioned above, by using $\gamma$-alumina "Neobead C" as a catalyst carrier. The resultant catalyst contained 2.1 parts by weight of ruthenium per 100 parts by weight of said alumina.

CATALYST 2 (Iron-Potassium-Copper/Alumina)

3.6 g of iron nitrate ($Fe(NO_3)_2 \cdot 9H_2O$), 0.1 g of Copper nitrate ($Cu(NO_3)_2 \cdot 3H_2O$) and 0.05 g of potassium nitrate ($KNO_3$) were dissolved in 5.0 ml of water. The resulting solution was added to 10 ml of a $\gamma$-alumina (Classification of Carrier A). After the mixture was allowed to stand overnight at room temperature, it was dried at 110° C. for 2 hours and was calcined at 450° C. in air for 4 hours. The resultant catalyst 2 contained 4.8 parts by weight of iron, 0.2 part by weight of copper and 0.2 part by weight of potassium.

CATALYST 3 (Ruthenium/Silica gel)

0.5 g of ruthenium chloride ($RuCl_3 \cdot H_2O$) was dissolved in 5.5 ml of water. The resulting solution was added to 10 ml of a silica gel (Classification D). After the mixture was allowed to stand overnight at room temperature, it was dried at 110° C. for 2 hours and was calcined at 450° C. in air for 4 hours. The resultant catalyst contained 2.1 parts by weight of ruthenium per 100 parts by weight of the above described silica gel. The catalysts belonging to Classification of Carriers E, F and so on (Table 1) were also prepared by the method similar to that described above. Each catalyst contained 1.6~2.2 parts by weight of ruthenium per 100 parts by weight of a $\gamma$-alumina.

COMPARATIVE CATALYST 3 (Ruthenium/Silica gel)

A comparative catalyst 3 was prepared by the same method as that described in example 3, by using silica gel "Davison RD type" as a catalyst carrier. The resultant catalyst contained 2.2 parts by weight of ruthenium per 100 parts by weight of said silica gel.

EXAMPLE OF REACTION

Fisher-Tropsch experiments were carried out by using a flow system having a vertical reactor 30 ml in inner volume.

For the production of hydrocarbons, all catalysts were pretreated by reducing in flowing hydrogen at flow rate of 50~60 ml/min. at 300° C. for 2 hours under atmospheric pressure. The experiments for the production of hydrocarbons were done by passing a mixture of hydrogen and carbon monoxide ($H_2/CO$ ratio of 0.5~3.0) over a catalyst at a pressure of about 8~15 $Kg/cm^2G$ and at each temperature of 235° C., 250° C., 275° C. or 300° C. The products were analyzed by a GCL measurement.

Figure 2:
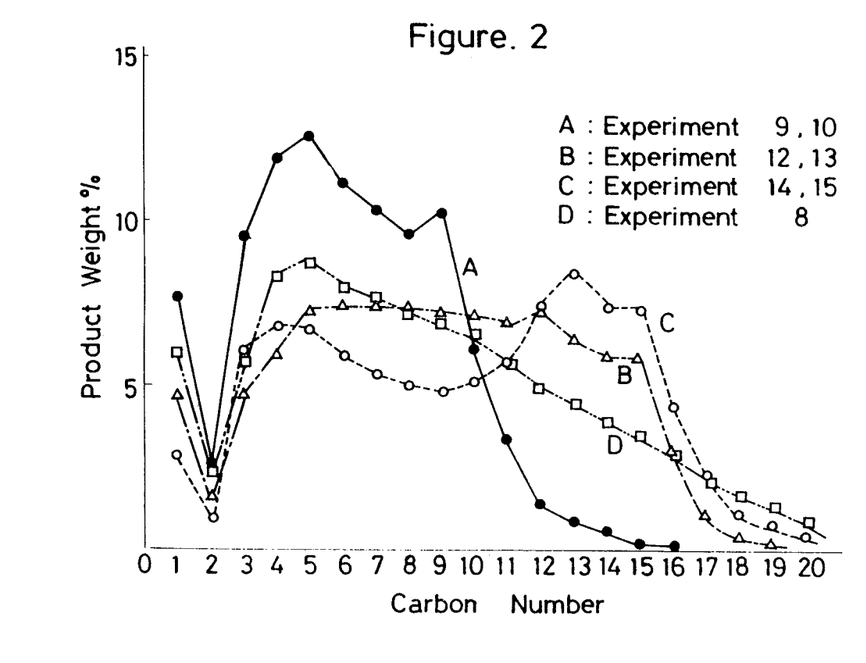
FIG. 2 is a graph of the product distribution of formed hydrocarbons which was obtained in the invention.

The catalysts which were prepared by the above-described method were tested at 235° C. and at a pressure of 10 $Kg/cm^2G$. and at a gas space velocity of 750 $hr^{-1}$ with a mixture of hydrogen and carbon monoxide having a $H_2/CO$ ratio of 1.0. The result is shown in Table 2. Herein, as a comparative example, the distribution of formed hydrocarbons obtained by using comparative catalyst 1 is shown in Exp. No. 8, and that obtained by using comparative catalyst 3 is shown in Exp. No. 16 of the Table. The detailed distribution of formed hydrocarbons by using each catalyst of Exp. 9, 12 and 14, and by using comparative catalyst 1 is shown in FIG. 2, which is the graph with the weight distribution of products on the vertical axis and the carbon number of formed hydrocarbons horizontally. For the catalyst 2, CO conversion was 31.5% and $CO_2$ selectivity was 26.0%. The weight distribution of formed hydrocarbons was similar to that of Experiment No. 1 except that the amount of $C_2$~$C_4$ hydrocarbons was 27 weight % of the total products.

TABLE 2

| Exp. No. | Classification of Carrier | | Temp. °C. | $H_2/CO$ Ratio V/V | CO Conversion (%) | $CO_2$ Selectivity (%) | Formed Hydrocarbon Wt % | | | | |
|---|---|---|---|---|---|---|---|---|---|---|---|
| | | | | | | | $C_1$ | $C_2$~$C_4$ | $C_5$~$C_{10}$ | $C_{11}$~$C_{15}$ | $C_{16}$~$C_{20}$ |
| 1 | A | $\gamma$-Alumina | 235 | 1 | 17.1 | — | 4.9 | 15.6 | 52.6 | 25.1 | 1.8 |
| 2 | | $\gamma$-Alumina | 235 | 1 | 13.8 | 2.8 | 5.4 | 14.8 | 50.8 | 27.6 | 1.4 |
| 3 | B | $\gamma$-Alumina | 240 | 1 | 27.6 | 1.3 | 3.3 | 13.6 | 44.2 | 35.1 | 3.8 |
| 4 | | $\gamma$-Alumina | 242 | 1 | 14.8 | 4.2 | 5.2 | 12.8 | 41.6 | 37.4 | 3.0 |
| 5 | C | $\gamma$-Alumina | 235 | 1 | 12.6 | 3.8 | 3.4 | 8.8 | 26.5 | 31.1 | 30.2 |
| 6 | | $\gamma$-Alumina | 241 | 1 | 13.8 | — | 2.9 | 9.0 | 28.7 | 28.8 | 30.6 |
| 7 | | $\gamma$-Alumina | 240 | 1 | 16.7 | — | 3.8 | 9.2 | 32.2 | 27.1 | 27.7 |
| 8 | | NEOBEAD C (Alumina) | 235 | 1 | 13.4 | 4.3 | 6.0 | 16.4 | 43.2 | 22.4 | 12.0 |
| 9 | D | Silica gel | 235 | 1 | 9.3 | — | 7.7 | 23.5 | 62.3 | 5.8 | 0.7 |
| 10 | | silica gel | 236 | 1 | 7.8 | — | 9.5 | 21.2 | 65.5 | 3.6 | 0.2 |
| 11 | | Silica gel | 235 | 1 | 13.6 | 0 | 6.9 | 20.3 | 62.0 | 9.2 | 1.6 |
| 12 | E | Silica gel | 240 | 1 | 12.4 | 4.2 | 4.5 | 12.1 | 37.2 | 40.9 | 5.3 |
| 13 | | Silica gel | 242 | 1 | 23.8 | — | 2.8 | 13.4 | 32.6 | 40.8 | 10.4 |

TABLE 2-continued

| Exp. No. | Classification of Carrier | | Temp. °C. | $H_2/CO$ Ratio V/V | CO Conversion (%) | $CO_2$ Selectivity (%) | Formed Hydrocarbon Wt % | | | | |
|---|---|---|---|---|---|---|---|---|---|---|---|
| | | | | | | | $C_1$ | $C_2\sim C_4$ | $C_5\sim C_{10}$ | $C_{11}\sim C_{15}$ | $C_{16}\sim C_{20}$ |
| 14 | F | Silica gel | 235 | 1 | 19.3 | 2.3 | 4.7 | 13.3 | 37.5 | 21.3 | 23.2 |
| 15 | | Silica gel | 241 | 1 | 21.6 | — | 4.5 | 13.3 | 33.2 | 28.6 | 20.4 |
| 16 | | Davison RD | 235 | 1 | 8.3 | 0 | 8.7 | 26.3 | 41.8 | 16.9 | 6.3 |

The results summerized in Table 1, Table 2, FIG. 1 and FIG. 2 are as follows:

(1) As can be seen by comparison of experiments 1, 2 and 8 of Table 2, the product distribution which was obtained in experiment 1 and 2, wherein the γ-alumina belonging to Classification A (Table 1) was used as a catalyst carrier, shows high selectivity to $C_5\sim C_{10}$ products and at the same time it also shows that the amount of hydrocarbons having high boiling point in the range $C_{16}\sim C_{20}$ is very small, whereas the product distribution in experiment 8 wherein the comparative catalyst 1 was used does not show such a high selectivity. As can be also seen by comparison of experiments 9, 10, 11 and 16 of Table 2, the selectivity of $C_5\sim C_{10}$ products which were obtained in experiment 9, 10 and 11 wherein the silica gel belonging to Classification D (Table 1) was used as a catalyst carrier, exceeded 65% of the total products by weight and at the same time the amount of $C_{11}\sim C_{15}$ and $C_{16}\sim C_{20}$ products was extremely small, whereas the selectivity of products in experiment 16 was not so high, wherein the comparative catalyst 3 was used. These results can be also indicated in the curve A of FIG. 2. Herein this curve shows that drastic decline in chain growth probability occurred at $C_9$.

(2) As can be seen by comparison of experiments 3, 4 and 8, the selectivity of $C_{11}\sim C_{15}$ products which was obtained in experiment 3 and 4, wherein the γ-almina belonging to classification B (Table 1) was used as a catalyst carrier, is high and at the same time the amount of the hydrocarbons having high boiling point in the range $C_{16}\sim C_{20}$ is small, whereas the selectivity of the products in experiment 8 is not so high. As can be also seen by comparison of experiments 12, 13 and 14, the selectivity of $C_{11}\sim C_{15}$ products which was obtained in experiment 12 and 13, wherein the silica gel belonging to Classification E (Table 1) was used as a catalyst carrier, is high, i.e. more than 40% of the total products by weight, compared that in experiment 16. This result can be also indicated in the curve B of FIG. 2. Herein this curve shows that drastic decline in chain growth probability occurs at $C_{15}$.

(3) As can be seen by comparison of experiments 5, 6, 7 and 8, the selectivity of $C_{16}\sim C_{20}$ products which was obtained in experiments 5, 6 and 7, wherein the γ-alumina belonging to Classification C was used as a catalyst carrier, is high, i.e. more than 30% of the total products by weight, compared with that in experiment 8. As can be also seen by comparison of experiments 14, 15, and 16, the selectivity of $C_{16}\sim C_{20}$ products which was obtained in experiments 14 and 15 wherein the silica gel belonging to Classification F was used as a catalyst carrier, is high, compared with that in experiment 16. This result can be also indicated in the Curve C of FIG. 2. Herein this curve shows that the chain growth probability increase in the range of high boiling point.

EXAMPLE 2

Figure 4:
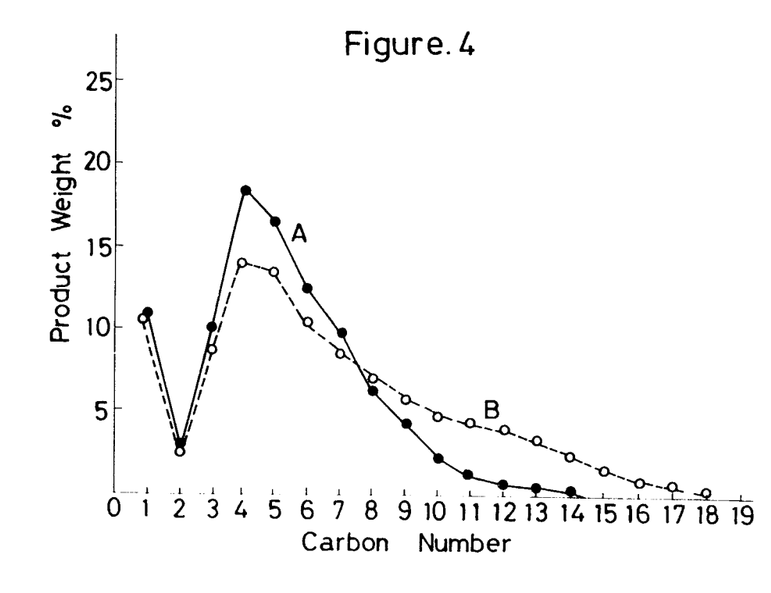
FIG. 4 is a graph of a product distribution of formed hydrocarbons which was obtained in the invention.

0.5 g of ruthenium chloride ($RuCl_3 \cdot H_2O$) was dissolved in 5 ml of water. The resulting solution was added to 10 ml of silica.alumina (surface area 470 m²/g, pore volume 0.25 ml/g, average pore radius 10.66 Å, the pore diameter having the largest differential pore volume, 14.0 Å). After the mixture was allowed to stand overnight at room temperature, it was dried at 110° C. for 3 hours and was calcined at 450° C. in air for 4 hours. The resultant catalyst contained 1.4 parts by weight of ruthenium per 100 parts by weight of above-described silica alumina. The Fisher-Tropsch experiment was carried out by using a flow system having a reactor 30 ml in inner volume. For the production of hydrocarbons, the catalyst was pretreated by reducing in flowing hydrogen at flow rate of 50~60 ml/min. at 300° C. for 2 hours under atmospheric pressure. The experiment was done by passing a mixture of hydrogen and carbon monoxide ($H_2/CO$ ratio 0.5~3.0) at a pressure of about 8~15 kg/cm²G and at each temperature of 235° C., 275° C. and 300° C. The products were analyzed by a GCL measurement. CO conversion and $CO_2$ selectivity were 18.3% and 4.3% respectively at 235° C., 27.4% and 8.8% respectively at 275° C. and 46.2% and 9.6% respectively at 300° C. The product distribution which was obtained at 235° C. in the above experiment is shown in FIG. 4, compared with that obtained by using commercially available silica.alumina as a catalyst carrier (comparative example). In the Figure, A indicates the product distribution obtained in the invention and B indicates that obtained in comparative example. As can be seen in FIG. 4, the product distribution curve which was obtained in the invention shows high selectivity to hydrocarbons having less than 10 of carbon number, preferably to $C_4\sim C_{10}$ hydrocarbons, and at the same time it shows the amount of hydrocarbons having more than 10 of carbon number is very small.

EXAMPLE 3

The catalyst was prepared by the same method used in Example 2 except that silica.alumina (surface area 417 m²/g, pore volume 0.29 ml/g, average pore radius 13.7 Å, the pore diameter having the largest differential pore volume 3.4 Å) was used as a catalyst carrier. The obtained catalyst contained 2.1 parts by weight of ruthenium per 100 parts by weight of above-described silica alumina. A Fisher-Tropsch experiment was carried out under the same reaction conditions as used in Example 2. The composition by weight of formed hydrocarbons obtained at 235° C. is 12.9% methane, 3.2% $C_2$, 10.7% $C_3$, 18.8% $C_4$, 16.4% $C_5$, 12.1% $C_6$, 9.1% $C_7$, 5.4% $C_8$, 3.3% $C_9$, 2.5% $C_{10}$ and 5.6% hydrocarbons having more than 11 of carbon number. CO conversions were 21.3% at 235° C. and 30.6% at 275° C. The amount of branched $C_7$, hydrocarbons is 52% by weight of total $C_7$ hydrocarbons.

COMPARATIVE EXAMPLE

The catalyst was prepared by the same method used in Example 2 except the use of a commercially available silica.alumina (surface area 421 m²/g, pore volume 0.43 ml/g measured with a high pressure mercury porosity meter, pore size distribution; 33% in the range of less than 70 Å, 33% in the range of 70~100 Å and 30% in the range of more than 200 Å). The obtained catalyst contained 1.8 parts by weight of ruthenium per 100 parts by weight of above-described silica alumina. A Fisher-Tropsch experiment was carried out under the same reaction conditions as used in Example 2. CO conversions were 17.2% at 235° C. and 33.2% at 275° C.

FIG. 4 shows the product distribution curve with the above catalyst.

EXAMPLE 4

The catalyst was prepared by the same method used in Example 2 except the use of a silica alumina (surface area 326 m²/g, pore volume 0.21 ml/g, average pore radius 12.7 Å, the pore diameter having the largest differential pore volume 14.2 Å). Thus obtained catalyst was impregnated with 5 ml of water containing 0.4 g of potassium nitrate and then dried. The catalyst prepared with the above method contained 1.8 parts by weight of ruthenium and 3.3 g by weight of potassium per 100 parts by weight of the above silica alumina. A Fisher-Tropsch experiment was carried out under the same reaction condition as used in Example 2. CO conversions were 13.6% at 235° C., 33.4% at 275° C. The formed hydrocarbons obtained at 235° C. included 5.3% of methane, 16.3% of $C_2$~$C_4$, 51.3% of $C_5$~$C_{10}$, 25.5% of $C_{11}$~$C_{15}$ and 1.6% of $C_{16}$~$C_{20}$. As shown from the above-obtained result the selectivity to $C_5$~$C_{10}$ hydrocarbons is high and the amount of $C_{16}$~$C_{20}$ hydrocarbons having high boiling point is small, whereas each selectivity of the products obtained by using the catalyst supported on the γ-alumina which does not have ordinary acidity, is low.

What we claim is:

1. A method for producing hydrocarbons, which comprises contacting synthesis gas having a molar ratio of hydrogen to a combined amount of at least one of carbon monoxide and carbon dioxide of from 0.5 to 3.0 with a heterogeneous catalyst at a temperature of from 200° to 350° C. and at a pressure of rom 0 to 100 Kg/cm²A and at a gas space velocity of from 500 to 5000 l/hour, said heterogeneous catalyst comprising 0.1 to 50 parts by weight of at least one VIII group metal capable of reducing at least one of carbon monoxide and carbon dioxide supported on 100 parts by weight of a metal oxide carrier having a very narrow pore size distribution in the micropores region within the range of between substantially 10 and 100 Angstroms.

2. The method for producing hydrocarbons according to claim 1, wherein said carrier is mixed metal oxides.

3. A method for producing hydrocarbons, which comprises contacting synthesis gas having a ratio of hydrogen to a combined amount of at least one of carbon monoxide and carbon dioxide from 0.5 to 3.0 with a heterogeneous catalyst at a temperature of from 200° to 350° C. and at a pressure of from 0 to 100 Kg/cm²A and a gas space velocity of from 500 to 5000 l/hour, said heterogeneous catalyst comprising 0.1 to 50 parts by weight of at least one VIII group metal capable or reducing at least one of carbon monoxide and carbon dioxide and 0.1 to 17 parts by weight of an alkali metal supported on 100 parts by weight of a mixed metal oxide carrier having a very narrow pore size distribution of the micropores region within the range of between 10 and 100 Angstroms.

4. The method for producing hydrocarbons according to claim 1, 2 and 3, wherein the narrow pore size distribution of carrier is located within the range of between 1~30 Angstroms.

5. The method for producing hydrocarbons according to claim 1, wherein the metal oxide carrier is selected from the group consisting of alumina and silica gel.

6. The method for producing hydrocarbons according to claims 2 or 3, wherein the mixed metal oxide carrier is selected from the group consisting of silica alumina and silica magnesia.

7. A method for selectively producing hydrocarbons useful in the manufacture of gasoline, kerosene and light oil, which comprises contacting synthesis gas having a molar ratio of hydrogen to a combined amount of at least one of carbon monoxide and carbon dioxide of from 0.5 to 3.0 with a heterogeneous catalyst at a temperature of from 200° to 350° C. and at a pressure of from 0 to 100 Kg/cm²A and at a gas space velocity of from 500 to 5000 l/hour, said heterogeneous catalyst comprising 0.1 to 50 parts by weight of at least one VIII group metal capable of reducing at least one of carbon monoxide and carbon dioxide supported on 100 parts by weight of a metal oxide carrier having a very narrow pore size distribution in the micropores region within the range of between substantially 10 to 100 Angstroms.

* * * * *